United States Patent [19]

Minnock et al.

[11] Patent Number: 5,393,888
[45] Date of Patent: Feb. 28, 1995

[54] NON-CATALYTIC LIQUID PHASE CONVERSION OF BUTYROLACTONE AND AMMONIA TO 2-PYRROLIDONE PRODUCT IN HIGH YIELD AND SELECTIVITY

[75] Inventors: Francis B. Minnock, West Orange, N.J.; Paul D. Taylor, Dublin, Ohio

[73] Assignee: ISP Investments Inc., Wilmington, Del.

[21] Appl. No.: 204,577

[22] Filed: Mar. 2, 1994

[51] Int. Cl.$^6$ ............................................ C07D 201/08
[52] U.S. Cl. .................................... 548/554; 548/543
[58] Field of Search ................................ 548/543, 554

Primary Examiner—David B. Springer
Attorney, Agent, or Firm—Marilyn J. Maue; Joshua J. Ward

[57] ABSTRACT

This invention relates to a liquid phase process for producing 2-pyrrolidone in high yield and selectivity in the absence of catalyst and extraneous solvents which involves contacting ammonia with butyrolactone in a molar ratio of from 0.5:1 to 0.85:1 at high temperature and pressure sufficient to maintain the liquid phase.

10 Claims, No Drawings

NON-CATALYTIC LIQUID PHASE CONVERSION OF BUTYROLACTONE AND AMMONIA TO 2-PYRROLIDONE PRODUCT IN HIGH YIELD AND SELECTIVITY

BACKGROUND OF THE INVENTION

Current commercial processes for the preparation of 2-pyrrolidone (2-pyrol) can be carried out in the liquid phase under a pressure of about 2,000 psig as is disclosed in U.S. Pat. No. 3,350,784 and British Patent 1,312,463; however liquid phase processes are generally associated with low pyrrolidone (pyrol) product yield, about 10% of the starting material being lost to dehydrated pyrol dimer by-product and other by-products which are difficult to analyze. Most often those impurities are included in the yield of 2-pyrol reported by the art. Liquid phase processes are also associated with the formation of other contaminating by-products such as 4-(N-pyrrolidonyl) butyramide (PBA), tetrahydrofuran and hydroxyalkyl butyramides which are derived from 4-hydroxy butyramide (HBA) intermediate. The formation of significant amounts of PBA impurity in current processes unavoidably takes place because of the cleavage of the lactone ring to form the intermediate which subsequently undergoes ring closure with the elimination of water to produce a crude product. It has been found that high dissolution of the reaction mixture may reduce the formation of by-product to some extent; however, this solution is not commercially attractive since a significantly larger reactor capacity is required and added costs are incurred by diluent separation.

Other objections to the liquid phase reaction involve lengthly reaction time of from 6 to 10 hours. To overcome some of the above difficulties, vapor phase reactions of lactone and ammonia have been proposed, examples of which are illustrated in U.S. Pat. Nos. 4,824,967 and 3,136,780. However, these vapor phase reactions require the use of a particulate silicate catalyst which requires separation and regeneration and in which product, along with impurities, can be entrapped, thus representing a considerable loss in recoverable product.

Although some prior processes achieve high conversion of butyrolactone, the crude product has been found to be highly contaminated with the above impurities and may also contain other contaminants which cannot be removed by fractional distillation and which require an additional acid treatment for product purification, as described in U.S. Pat. 3,140,294.

Accordingly, it is an object of this invention to provide a commercially feasible liquid phase process for the reaction of butyrolactone and ammonia to produce 2-pyrrolidone in high yield and selectivity within a relatively short reaction period.

Another object of the invention is to provide a process for the preparation of 2-pyrrolidone which minimizes contamination so that, for certain purposes, the separation of unwanted by-products may not be necessary.

Still another object is to provide a process which may be carried out in a batch or a continuous method and in the absence of extraneous solvents and catalyst.

THE INVENTION

In accordance with this invention there is provided a process for minimizing the concentration of HBA intermediate during the reaction by observance of a critical weight ratio of γ-butyrolactone (BLO) to ammonia, namely a molar ratio of between 1:0.5 and 1:0.85, preferably between about 1:0.6 and about 1:0.7. No advantage is realized using a higher excess of BLO reactant. Although higher excess of BLO can be employed without detriment to the reaction, increased volume requires larger reactor capacity. By observing the above critical excess of BLO, the normal production of intermediate hydroxybutyramide, which is the source of several secondary by-product reactions, can be substantially reduced so that such side reactions normally associated with HBA are minimized or fail to occur.

Generally, the lactone reactant can be introduced with water as an aqueous 5–20 weight % BLO solution; although anhydrous BLO can also be employed as feed in the present reaction. When an aqueous solution of BLO is used, the mole ratio of $H_2O$ to BLO is between about 1:5 and about 2:1, preferably an aqueous solution containing between about 5 and about 12 wt. % water is used. The ammonolysis reaction is carried out at a temperature of between about 200° and about 375° C. since below 200° C., the reaction is too slow for industrial production and above 350° C., the concentration of liquid impurities and residue begins to increase, thus giving rise to low selectivity and product contamination. The reaction is maintained under a pressure of from about 700 to about 1,800 psi and the reactants are physically or mechanically mixed for a period of from about 10 minutes to about 2.5 hours during which ammonia is consumed and conversion to 2-pyrrolidone product takes place. The preferred reaction parameters include a temperature of from about 275° to about 325° C. and a pressure of from about 800 to about 1,500 psi.

It is beneficial in the above reaction to add liquid ammonia in selected increments or gradually throughout the mixing operation so as to minimize the concentration of HBA at all times during reactant contact.

As referred to above, the present reaction can be carried out in a batch or continuous manner. The batch operation is effected over a period of from about 10 minutes to about 2 hours, more often from about 15 minutes to about 1 hour. In a continuous operation the aqueous or anhydrous butyrolactone is fed to the reactor at a rate of from about 1.0 to about 6.0, preferably 1.33–4.0, vols/hr. with gradual or multiple point introduction of ammonia to maintain the critical weight ratio of reactants defined above and thus minimize HBA formation. Product is recovered in a yield and a selectivity of BLO to 2-pyrrolidone greater than 93%.

A further advantage in the above process is achieved by using reverse order distillation for product recovery where high boiling and non-volatile impurities are first removed in a distillation column from distillate containing pyrrolidone, water and some low boiling impurities. Pyrrolidone is then separated from water and the remaining low boiling impurities in a second distillation column wherein the pyrrolidone product is recovered from the column reboiler. This reverse order distillation procedure provides the highest and purest yield of product.

Having thus generally described the invention, reference is now had to the accompanying Examples which illustrate preferred embodiments thereof but which are not construed as limiting to the scope of the invention as more broadly described above and in the appended claims. In the Examples, all proportions and amounts are by weight.

EXAMPLE 1

Continuous Process

A mixture of 90 wt. % γ-butyrolactone (BLO) and 10 wt. % water was preheated to 300° C. and introduced at a rate of 1816 g/hr. to a tubular, stainless steel reactor (80 feet in length) which was immersed in an oil bath to maintain a reaction temperature at 310° C. and was equipped with a control to maintain a pressure in the reactor of 1,500 psi. Liquid ammonia was introduced at 3 equidistant feed points along the reactor tube. The ammonia was pumped into the reactor at a total rate of about 194 g/hr. to achieve a final equivalent $NH_3$ to BLO molar ratio of 0.6:1.

The collected product showed a 94% selectivity of BLO to pyrrolidone and 100% conversion of $NH_3$.

Only about 1% lower product conversion and selectivity were achieved when anhydrous BLO was substituted in the above example.

EXAMPLE 2

Batch Process

Into a stainless steel autoclave equipped with a mechanical stirrer and maintained at 325° C. under 1,000 psi was introduced 2350 g. of an aqueous BLO solution (2100 g. in 250 g. $H_2O$. After reaction temperature was reached, liquid ammonia was introduced in 2 increments of 125 g. each, about 10 minutes apart to achieve an ammonia to BLO mole ratio of about 0.6:1. The reaction mixture was agitated for an additional 15 minutes at 325° C. before cooling to room temperature and removing product. The selectivity of BLO to pyrrolidone was found to be 97%.

Only about 2% lower product selectivity was obtained when anhydrous BLO was substituted in this example.

EXAMPLE 3

Purification of Product from Example 1

About 1 cc/minute of the product from Example 1 is continuously fed to a 1 inch Oldershaw column having 10 stages above the point of feed and 20 stages below said feed introduction. The higher boiling impurities, such as 4(2-pyrrolidonyl) butyric acid, 4-butyronitrile-2-pyrrolidone and 4-butyroamide-2-pyrrolidone, are continuously removed from the bottom of the column and the mixture of water, 2-pyrrolidone and low boiling compounds such as γ-butyrolactone, butanediol and ammonia are recovered overhead.

The column overhead is then introduced into a second 1 inch Oldershaw column having 20 stages above and 20 stages below the point of feed and the product in 98 to 99% yield based on BLO is continuously recovered from the bottom of the second column in higher than 99.9% pure 2-pyrrolidone which has a pale yellow color. Although, this slight degree of color can be removed, if desired, by using a vapor draw-off from which bottoms are separately recovered. The unreacted butyrolactone can be recycled as feed to the reactor for further economy.

EXAMPLE 4 (COMPARATIVE)

Example 1 was repeated several times except that in each instance 1000 g./hr. of BLO and 217 g./hr. of ammonia were charged to the reactor to provide a BLO to $NH_3$ ratio of 1:1.1. The selectivity to 2-pyrrolidone product dropped to between 85 and 87%.

What is claimed is:

1. In a liquid phase process for reacting ammonia and γ-butyrolactone at high temperature and high pressure to form 2-pyrrolidone, the improvement which comprises employing a mole ratio of ammonia to butyrolactone between about 0.5:1 and 0.85:1 in the reaction to form a substantially contaminant free 2-pyrrolidone product.

2. The process of claim 1 wherein the mole ratio of ammonia to butyrolactone is between 0.6:1 and 0.7:1.

3. The process of claim 1 wherein the excess of butyrolactone is maintained throughout the reaction by controlled gradual or incremental addition of liquid ammonia during reaction.

4. The process of claim 1 wherein the γ-butyrolactone is introduced in the anhydrous state.

5. The process of claim 1 wherein the γ-butyrolactone is introduced as an aqueous solution wherein the mole ratio of water to butyrolactone is between about 1:5 and about 2:1.

6. The process of claim 5 wherein said ammonia reactant is added in increments throughout the reaction.

7. The process of claim 1 wherein said product is first distilled in a first stage to remove contaminants boiling above 2-pyrrolidone and then separately distilled in a second stage to remove contaminants boiling below 2-pyrrolidone.

8. The process of any one of claims 1–7 in which the reaction is carried out at a temperature of from about 200° to about 375° C. under a pressure of from about 700 to about 1,800 psi.

9. The 2-pyrrolidone product of the process of any one of claims 1 to 7 in a purity greater than 85%.

10. The 2-pyrrolidone product of the process of claim 7 in greater than 99.5% purity.

* * * * *